US006770774B2

(12) United States Patent
Van De Bovenkamp-Bouwman et al.

(10) Patent No.: US 6,770,774 B2
(45) Date of Patent: Aug. 3, 2004

(54) PEROXIDES, THEIR PREPARATION PROCESS AND USE

(75) Inventors: Anna Gerdine Van De Bovenkamp-Bouwman, Nijkerk (NL); Joachim Willem J. Van Gendt, Luttenberg (NL); John Meijer, Deventer (NL); Bart Fischer, Leusden (NL); Andreas Herman Hogt, Enschede (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 10/278,402

(22) Filed: Oct. 23, 2002

(65) Prior Publication Data

US 2003/0073861 A1 Apr. 17, 2003

Related U.S. Application Data

(62) Division of application No. 09/673,443, filed as application No. PCT/EP99/02643 on Apr. 13, 1999, now Pat. No. 6,482,970.

(30) Foreign Application Priority Data

Apr. 15, 1998 (EP) ............................................ 98201170

(51) Int. Cl.$^7$ .............................................. L07C 69/96
(52) U.S. Cl. ........................ 558/265; 558/266; 568/561
(58) Field of Search ................................ 558/260, 263, 558/265, 266; 568/558, 561, 567

(56) References Cited

U.S. PATENT DOCUMENTS

| | | | |
|---|---|---|---|
| 3,652,631 A | * | 3/1972 | Stevens et al. |
| 3,706,818 A | * | 12/1972 | Mageli et al. |
| 3,775,465 A | | 11/1973 | Sacrini et al. ........ 260/475 SC |
| 3,839,390 A | | 10/1974 | D'Angelo et al. ...... 260/453 R |
| 3,846,396 A | | 11/1974 | D'Angelo et al. ... 260/94.9 GA |
| 4,097,408 A | | 6/1978 | Sanchez ..................... 252/426 |
| 4,129,704 A | | 12/1978 | Sanchez ...................... 526/73 |
| 5,973,181 A | * | 10/1999 | Ishigaki et al. ............. 558/263 |
| 6,552,215 B1 | * | 4/2003 | Van De Bovenkamp-Bouwman et al. .......... 558/263 |

FOREIGN PATENT DOCUMENTS

| | | | |
|---|---|---|---|
| FR | 2 376 844 | 4/1978 | ......... C07C/179/18 |
| JP | 48-43491 | 6/1973 | |
| JP | 50-23079 | 3/1975 | |

OTHER PUBLICATIONS

CA:67:90784 abs of Chemisch Berichte by Schulz et al 100(7) pp 2242–9 1967.*
CA:63:709602 abs of Zhurnal Obshchei Khimii by Kirillov A.I. 1(7) pp 1230–4 1965.*
Yoshikawa, Kanji, et al., "A Method of producing a peroxycarbonate," Patent Gazette No. 1973–43491, Dec. 29, 1973, p.p. 1–7.
Yoshikawa, Kanji, et al., "A method of polymerizing ethylene," Patent Gazette No. 1975–23079, Dec. 29, 1970, p.p. 1–12.
Razuvaev, G. A., et al., Thermal Decomposition of Bis(1–Methylpercarbonatocyclohexyl) Peroxides, Journal of General Chemistry USSR, vol. 33, 1963, p.p. 124–130.
Ol'dekop, Yu. A., et al., "1,1'–Bis(Acylperoxy)Dicyclohexyl Peroxides," Doklady Chemistry, vol. 139, 1961, p.p. 811–814.
Kirillov, A. I., "Reactions of Free Peroxidic Alkoxy Radicals Formed By The Decomposition Of Acylated Bis–(2–Hydroperoxybutyl) Peroxides," Journal of Organic Chemistry of the USSR, vol. 1, No. 7, 1965, p.p. 1241–1245.

* cited by examiner

Primary Examiner—Jean F. Vollano
(74) Attorney, Agent, or Firm—Richard P. Fennelly

(57) ABSTRACT

The invention relates to a preparation process for making peroxy esters and peroxy carbonates, peroxy ester peroxy carbonates, mixed diperoxides, mixed diperoxy esters, and mixed diperoxy carbonates, and to specific monoperoxy esters, monoperoxy carbonates, mixed peroxides, mixed diperoxy esters, mixed diperoxy carbonates, peroxy ester peroxy carbonates, and mixtures thereof. The process involves the reaction of a type-3 ketone peroxide with a reactive carbonyl compound and optional subsequent reaction with an alkyl vinyl ether, acetal, halogen formate, or carboxylic acid anhydride.

8 Claims, No Drawings

PEROXIDES, THEIR PREPARATION PROCESS AND USE

This application is a divisional of U.S. Ser. No. 09/673,443 now U.S. Pat. No. 6,482,970, filed Nov. 28, 2000, which application is a national phase filing of PCT/EP99/02643, having an international filing date of Apr. 13, 1999 and which claims priority from European Patent Application Serial No. 98201170.2, filed Apr. 15, 1998.

The present invention relates to particular peroxides, mixtures comprising one or more of these peroxides, their preparation process, and their use. More particularly, the present invention relates to the preparation process of peroxy esters and peroxy carbonates, peroxy ester peroxy carbonates, mixed diperoxides, mixed diperoxy esters, and mixed diperoxy carbonates, and to specific monoperoxy esters, monoperoxy carbonates, mixed peroxides, mixed diperoxy esters, mixed diperoxy carbonates, peroxy ester peroxy carbonates, and mixtures thereof. Finally, the present invention relates to the use of these peroxides as polymerization initiators, curing agents for unsaturated polyesters, and modifying agents, and to formulations comprising these peroxides.

JP-A-50-23079 discloses the production of symmetric peroxides by reacting a dialkyl ketone hydroperoxyde with an acyl chloride in a two-phase solvent system comprising a polar (aqueous) solvent and an apolar solvent. A monoperoxy ester or monoperoxy carbonate is not formed. The peroxy esters are used in the homopolymerization of ethylene or the copolymerization of ethylene and another ethylenically unsaturated monomer.

JP-A-48-43491 discloses a similar method for the production of diperoxy carbonates.

Because these prior art preparation processes do not result in the formation of monoperoxy ester or monoperoxy carbonate as a major constituent, it is not possible to produce asymmetric diperoxy esters, diperoxy carbonates, and mixed peroxides in a controlled manner.

It is an object of the present invention to provide a new class of monoperoxy esters and monoperoxy carbonates which on the one hand are useful as polymerization initiators, curing agents for unsaturated polyesters, and modifying agents, and on the other serve as a starting material for the production of a novel class of mixed peroxides, mixed diperoxy esters, mixed diperoxy carbonates, and peroxy ester peroxy carbonates which are also useful as polymerization initiators, curing agents for unsaturated polyesters, and modifying agents.

The present invention is based on the insight that by the proper selection of ketone peroxides on the one hand and acid halogen or halogen formate on the other, monoperoxy esters and monoperoxy carbonates are formed in an adjustable relative amount. These monoperoxy esters and monoperoxy carbonates in turn allow the provision of a new class of mixed peroxides, mixed diperoxy esters, mixed diperoxy carbonates, and peroxy ester peroxy carbonates.

Accordingly, the present invention provides a process for the preparation of monoperoxy ester or monoperoxy carbonate having the general formula I:

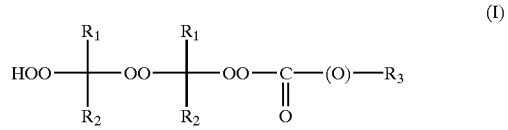

wherein $R_1$ and $R_2$ are independently selected from the group comprising hydrogen, $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, or $R_1$ and $R_2$ form a $C_3$–$C_{12}$ cycloakyl group, which groups may include linear or branched alkyl moieties, and each of $R_1$ and $R_2$ may optionally be substituted with one or more groups selected from hydroxy, alkoxy, linear or branched alkyl, aryloxy, halogen, ester, carboxy, nitrile, and amido, and $R_3$ is independently selected from the group comprising $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, which groups may include linear or branched alkyl moieties, and $R_3$ may optionally be substituted with one or more groups selected from hydroxy, alkoxy, linear or branched alkyl, aryloxy, halogen, ester, carboxy, nitrile, and amido, which process comprises the reaction of the corresponding ketone peroxide with the general formula II:

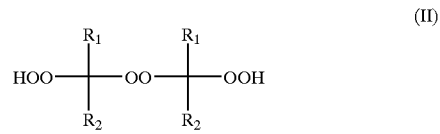

wherein $R_1$ and $R_2$ have the identified meaning, with a reactive carbonyl compound with the general formula III:

wherein $R_3$ has the identified meaning and L is a group activating a carbonyl group of the carbonyl compound (III) for reaction with the ketone peroxide (II), in an inert two-phase solvent system comprising a polar solvent and an apolar solvent. Ketone peroxides of formula II are also known as type-3 (T3) ketone peroxides.

The inert two-phase solvent system comprises a polar solvent and an apolar solvent. Preferably the polar solvent is an aqueous alkali comprising phase. The apolar solvent is not miscible with the polar solvent. A solvent is a polar solvent when its dipole moment is larger than 0D, and preferably larger than 0.5D, in other words, when it has a certain polarity. A solvent is an apolar solvent when its dipole moment is 0.5D or less, preferably essentially 0D. The apolar solvent has substantially no polarity.

Suitable polar solvents comprise alcohols, cycloalkanols, ethers, alkylene glycols, amides, aldehydes, ketones, esters, halogenated hydrocarbons such as chlorinated hydrocarbons, and mixtures thereof. The use of polar solvents like anhydrides, carbonates, and epoxides is less desired since they are not fully inert.

However, an aqueous (alkali) phase is preferred as the polar solvent.

Suitable apolar solvents generally are hydrocarbon solvents, aromatic hydrocarbon solvents, aralkyl solvents, paraffinic oils, white oils, and silicone oils, as well as their mixtures. Useful hydrocarbon solvents include, but are not limited to, benzene, xylene, toluene, mesitylene, hexane, hydrogenated oligomers of alkanes such as Isopar® products (ex. Exxon), Shellsol® products (ex Shell), pentane, heptane, decane, isododecane, decalin, and the like. Paraffinic oils useful as apolar solvents comprises for instance paraffinic diesel oil. Other oils, including white oils, epoxidized soybean oils, and silicone oils are also useful in the present invention.

By properly selecting the equivalent amount of the carbonyl compound used in the preparation process, the amount of monoperoxy ester and monoperoxy carbonate can be adjusted further. The amounts are preferably selected such that at least 10% by weight of the desired product is formed. More preferably such that at least 25% by weight of these products is formed. Even more preferably, the amount of acid halogen or halogen formate is in the range of 0.5–5 equivalents, so that the amount of monoperoxy ester and monoperoxy carbonate formed is at least 50% of the produced peroxides. Using 0.9–2.5 equivalents the selectivity is increased further. Most preferred is an equivalent amount in the range of 1–2 equivalents. Then the selectivity generally is above 60%, such as above 80% or even above 90%. This selectivity may be expressed in the mono:bis ratio.

The reaction conditions are conventional. The temperature generally is in the range of −10 to 50° C. and suitably between 0–30° C. A practical range is from 5 to 15° C. Essentially the temperature is selected such that side reactions and decomposition of the materials are avoided. The pH is basic, i.e. above 7. Generally, the pH is in the range of 9–14. In practice, the pH is above 10, and a practical range is from 11 to 13.5. The reaction proceeds under ambient pressure and in free contact with the atmosphere.

Suitable ketone peroxides for the reaction with the carbonyl compound are those derived from the following ketones: acetone, acetophenone, methyl-n-amyl ketone, ethylbutyl ketone, ethylpropyl ketone, methylisoamyl ketone, methylheptyl ketone, methylhexyl ketone, ethylamyl ketone, diethyl ketone, dipropyl ketone, methylethyl ketone, methylisobutyl ketone, methylisopropyl ketone, methylpropyl ketone, methyl-n-butyl ketone, methyl-t-butyl ketone, isobutylheptyl ketone, diisobutyl ketone, methoxy acetone, cyclohexanone, 2,4,4-trimethyl cyclo hexanone, N-butyllevulinate, ethylacetoacetate, methylbenzyl ketone, phenylethyl ketone, methylchloromethyl ketone, methylbromomethyl ketone, and coupling products thereof. Other ketones having the appropriate $R_1$ and $R_2$ groups corresponding to the peroxides of the formula II can also be employed.

L may be any group that activates the carbonyl group of the carbonyl compound for reaction with a hydroperoxide group of the ketone peroxide, and substantially does not interfere with this reaction. Suitable examples of L are halogen and the groups —O—$R_3$', —O—CO—$R_3$' and —O—CO—O—$R_3$'. $R_3$' is selected independently of $R_3$ from the same group of substituents as $R_3$. When L is halogen, the carbonyl compound (III) is an acid halogen or a halogen formate. When L is the group —O—$R_3$', the carbonyl compound (III) is a carboxylic acid ester or a carbonate. When L is the group —O—CO—$R_3$', the carbonyl compound (III) is a carboxylic acid anhydride or a mixed anhydride. When L is the group —O—CO—O—$R_3$' the carbonyl compound (III) is a pyrocarbonate or a mixed anhydride.

Preferred acid halogens comprise those wherein $R_3$ is a linear or branched $C_1$–$C_{12}$ alkyl, cycloalkyl, aryl, aralkyl, alkaryl group, the aryl group preferably being a phenyl group. Typical examples are the acid halogens obtainable from the following carboxylic acids: acetic acid, phenylacetic acid, phenoxyacetic acid, propanoic acid, isobutyric acid, benzoic acid, 2-methyl-benzoic acid, 2-methylbutanoic acid, 2-butenoic acid, 3-phenylpropenic acid, 2,2-dimethylpropanoic acid, 2,2-dimethylbutanoic acid, 2,2-dimethylpentanoic acid, 2-ethylbutanoic acid, 3,5,5-trimethylhexanoic acid, 2-ethylhexanoic acid, neohexanoic acid, neoheptanoic acid, neodecanoic acid, octanoic acid, nonanoic acid, lauric acid, 3,5,5-trimethylpentanedioic acid, hexanedioic acid, 3,5,5-trimethylhexanedioic acid, 2,4,4-trimethylhexanedioic acid, decanedioic acid, undecanedioic acid, dodecanedioic acid, cyclohexanecarboxylic acid, 1,4-cyclohexanedicarboxylic acid, cyclohexane-1,4-diacetic acid, maleic acid, citric acid, methylsuccinic acid, citraconic acid, fumaric acid, oxalic acid, terephthalic acid, propenoic acid, and phthalic acid, and their corresponding methyl esters, ethyl esters, n-propyl esters, isopropyl esters, n-butyl esters, sec-butyl esters, isobutyl esters, ethylene glycol esters, and propylene glycol esters. Preferably the halogen is chlorine.

Preferred halogen formates are chloroformates. Examples of the chloroformates used are: 2-(1-methylethoxy)phenyl chloroformate, 1-methylpropyl chloroformate, 4-methylphenyl chloroformate, 2,2,2-trichloro-1,1-dimethylethyl chloroformate, heptyl chloroformate, cyclohexylmethyl chloroformate, ethyleneglycol bis (chloroformate), 3-(1,1-dimethylethyl)phenyl chloroformate, 3-(trichlorosilyl)propyl chloroformate, phenyl chloroformate, 3-methoxybutyl chloroformate, 2-phenoxyethyl chloroformate, 2,2-dimethyl-1,3-propanediol bis(chloroformate), phenylmethyl chloroformate, 9-octadecenyl chloroformate, 2-methylphenyl chloroformate, bisphenol A bis (chloroformate), 1,3-dimethylbutyl chloroformate, 3,4-dimethylbutyl chloroformate, 3,4-dimethylphenyl chloroformate, trichloromethyl chloroformate, 1-chloroethyl chloroformate, chloromethyl chloroformate, 1,4-butanediol bis(chloroformate), 1,1-bis(ethoxycarbo) ethyl chloroformate, 3,5-dimethylphenyl chloroformate, octyl chloroformate, ethyl chloroformate, octadecyl chloroformate, (2-oxo-1,3-dioxolan-4-yl)methyl chloroformate, 1,6-hexanediol bis(chloroformate), 2-chlorobutyl chloroformate, 4-methoxyphenyl chloroformate, 2-methylpropyl chloroformate, 2-(methylsulfonyl)ethyl chloroformate, dodecyl chloroformate, 1,4-cyclohexanedimethanol bis (chloroformate), 2-chloro-2-phenylethyl chloroformate, 2-acryloyloxyethyl chloroformate, 4-nitrophenyl chloroformate, n-butyl chloroformate, decyl chloroformate, 2-ethylhexyl chloroformate, 2-propenyl chloroformate, 2-chlorocyclohexyl chloroformate, 2-methyl-2-propenyl chloroformate, cyclohexyl chloroformate, 2-chloroethyl chloroformate, [4-(phenylazo)phenyl]methyl chloroformate, hexadecyl chloroformate, 1-naphthalenyl chloroformate, 2-[2-cyclopentyl-4-(1,1-dimethylethyl)phenoxy]-1-methylethyl chloroformate, 3,5,5-trimethylhexyl chloroformate, isotridecyl chloroformate, tridecyl chloroformate, 4-(1,1-dimethylethyl)cyclohexyl chloroformate, 2,4,5-trichlorophenyl chloroformate, 3-chloropropyl chloroformate, tetradecyl chloroformate, 9H-fluoren-9-ylmethyl chloroformate, (4-nitrophenyl) methyl chloroformate, methyl chloroformate, 2-(1-methylethyl)phenyl chloroformate, triethyleneglycol bis (chloroformate), 2-methoxyethyl chloroformate, 1-methylethenyl chloroformate, 3-methylphenyl chloroformate, 2-bromoethyl chloroformate, diethyleneglycol bis(chloroformate), 3-methyl-5-(1-methylethyl)phenyl chloroformate, 2,2,2-tribromoethyl chloroformate, 2-ethoxyethyl chloroformate, 3-methyl-1,5-pentanediol bis (chloroformate), 4-methoxy carbophenyl chloroformate, ethenyl chloroformate, 1-methylethyl chloroformate, 2-(1-methylpropyl)phenyl chloroformate, 2,2,2-trichloroethyl chloroformate, pentyl chloroformate, cyclodecyl chloroformate, 4-(1,1-dimethylethyl)phenyl chloroformate, hexyl chloroformate, n-propyl chloroformate, 3-methoxy-3-methylbutyl chloroformate, 2-propoxyethyl chloroformate, 2-methoxy-1-methylethyl chloroformate, 2-butoxyethyl chloroformate, 2,2-dimethylpropyl chloroformate, 2,3-dihydro-2,2-dimethyl-7-benzofuranyl chloroformate, 1-chloroethyl chloroformate, cyclobutyl chloroformate, 5-methyl-2-(1-methylethyl)cyclohexyl chloroformate, 1,1-dimethylethyl chloroformate, 1-methylheptyl chloroformate.

Suitable carboxylic acid anhydrides or mixed anhydrides are those derived from the carboxylic acids: acetic acid, phenylacetic acid, phenoxyacetic acid, propanoic acid, isobutyric acid, benzoic acid, 2-methyl-benzoic acid, 2-methylbutanoic acid, 2-butenoic acid, 3-phenylpropenic acid, 2,2-dimethylpropanoic acid, 2,2-dimethylbutanoic acid, 2,2-dimethylpentanoic acid, 2-ethylbutanoic acid, 3,5, 5-trimethylhexanoic acid, 2-ethylhexanoic acid, neohexanoic acid, neoheptanoic acid, neodecanoic acid, octanoic acid, nonanoic acid, lauric acid, 3,5,5-trimethylpentanedioic acid, hexanedioic acid, 3,5,5-trimethylhexanedioic acid, 2,4,4-trimethylhexanedioic acid, decanedioic acid, undecanedioic acid, dodecanedioic acid, cyclohexanecarboxylic acid, 1,4-cyclohexanedicarboxylic acid, cyclohexane-1,4-diacetic acid, maleic acid, citric acid, 3-hydroxybutanoic acid, 4-hydroxybutanoic acid, 2-hydroxy-pentanoic acid, 3-hydroxypentanoic acid, 4-hydroxypentanoic acid, 5-hydroxypentanoic acid, hydroxyacetic acid, 2-hydroxyisobutyric acid, 2-hydroxypropanoic acid, 2-hydroxyhexanoic acid, hydroxypivalic acid, hydroxysuccinic acid, succinic acid, methylsuccinic acid, citraconic acid, fumaric acid, itacomic acid, oxalic acid, terephthalic acid, propenoic acid, and phthalic acid, and their corresponding methyl esters, ethyl esters, n-propyl esters, isopropyl esters, n-butyl esters, sec-butyl esters, isobutyl esters, ethylene glycol esters, and propylene glycol esters, and the halogen substituted carboxylic acids.

Suitable carboxylic acid esters, mixed anhydrides, and pyrocarbonates are those having the exemplified substituents of the acid halogens, halogen formates, and carboxylic acid anhydrides.

Preferably, the ketone peroxide is derived from methylethyl ketone, methylisopropyl ketone, methylisobutyl ketone, acetone, cyclohexanone, and/or 2,4,4-trimethylcyclohexanone, and the acid chloride is selected from the group comprising acetyl chloride, 2-ethylhexanoyl chloride, pivaloyl chloride, neodecanoyl chloride, neoheptanoyl chloride, and isobutyryl chloride, or the halogen formate is selected from the group comprising the chloroformates 2-ethylhexanoyl chloroformate, isopropyl chloroformate, sec.butyl chloroformate, ethylchloroformate, butylchloroformate, 4-tert.butyl cyclohexyl chloroformate, tetradecyl chloroformate, and hexadecyl chloroformate.

The monoperoxy esters and monoperoxy carbonates formed in the process according to the present invention may be used as starting materials for the preparation of typical mixed peroxides, mixed diperoxy esters, mixed diperoxy carbonates, and peroxy ester peroxy carbonates.

Accordingly, the present invention relates to monoperoxy ester or monoperoxy carbonate having the general formula I

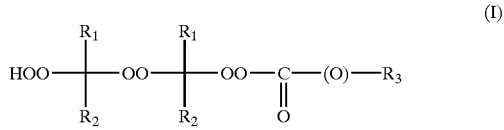

wherein $R_1$, $R_2$ and $R_3$ have the identified meaning and are obtainable with the process defined hereinbefore.

The invention further relates to a process for the preparation of the mixed peroxide having the general formula IV:

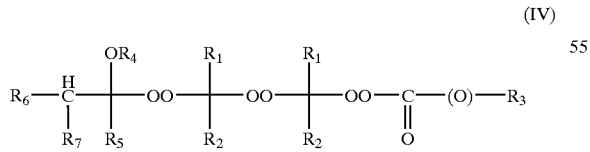

wherein $R_1$, $R_2$, $R_5$, $R_6$, and $R_7$ are independently selected from the group comprising hydrogen, $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, or $R_1$ and $R_2$ may form a $C_3$–$C_{12}$ cycloalkyl group, which groups may include linear or branched alkyl moieties, and each of $R_1$, $R_2$, $R_5$ $R_6$ and $R_7$ may optionally be substituted with one or more groups selected from hydroxy, alkoxy, linear or branched alkyl, aryloxy, halogen, ester, carboxy, nitrile, and amido, $R_3$ and $R_4$ are independently selected from the group comprising $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, which groups may include linear or branched alkyl moieties, and each of $R_3$ and $R_4$ may optionally be substituted with one or more groups selected from hydroxy, alkoxy, linear or branched alkyl, aryloxy, halogen, ester, carboxy, nitrile, and amido, wherein a monoperoxy ester or monoperoxy carbonate and any pair of the optionally substituted $R_4$, $R_5$, $R_6$, and $R_7$ may form a ring, which process comprises the reaction of the corresponding monoperoxy ester or monoperoxy carbonate with the general formula I:

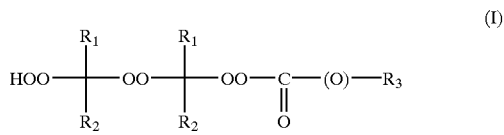

wherein $R_1$, $R_2$, and $R_3$ have the identified meaning, with an alkyl vinyl ether with the general formula Va, or an acetal with the general formula Vb:

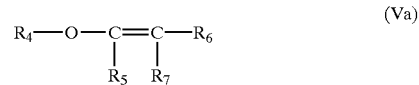

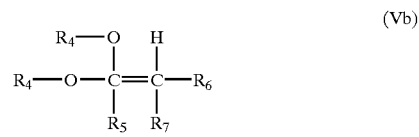

wherein $R_4$, $R_5$, $R_6$, and $R_7$ have the identified meaning, in the presence of an acid catalyst.

$R_5$, $R_6$, and $R_7$ preferably are hydrogen.

The monoperoxy ester or monoperoxy carbonate used in this process preferably is obtained in the above preparation process for these monoperoxy ester and monoperoxy carbonates.

The monoperoxy ester or monoperoxy carbonate is reacted with an alkyl vinyl ether or acetal with the general formula Va or Vb:

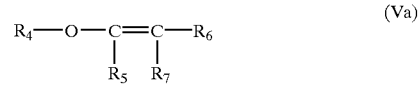

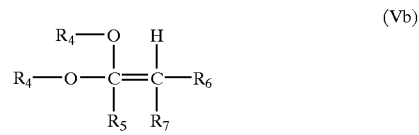

wherein the groups $R_4$, $R_5$, $R_6$, and $R_7$ have the meaning as specified above. $R_5$, $R_6$, and $R_7$ preferably are hydrogen.

Specific examples of the alkyl vinyl ether with the general formula Va are: vinyl 2,2-bis(vinyloxymethyl)butyl ether, 2-methoxy-2-butene, n-propyl vinyl ether, 1-ethoxy-4-methyl-1-nonene, tert.amyl vinyl ether, 2,2-bis(4-vinyloxyphenyl)propane, hexadecyl vinyl ether, methyl vinyl ether, 4-methylhexyl vinyl ether, 2-(2-ethoxyethoxy) ethyl vinyl ether, 2-methoxyethyl vinyl ether, 2-vinyloxy ethanol, 4-methyl-1-decenyl vinyl ether, benzyl 1-methyl vinyl ether, butanediol divinyl ether, tert.butyl vinyl ether, isobutyl vinyl ether, cyclohexanedimethanol divinyl ether, cyclohexyl vinyl ether, ethyleneglycol divinyl ether, 1-ethoxy-4-(1-ethoxyvinyl)-3,3,5,5-tetramethylcyclohexene, isopropyl vinyl ether, ethyl vinyl ether, tetraethyleneglycol divinyl ether, 1,1,3-trimethoxypropene, 1-methoxy-1-buten-3-yne, heptyl vinyl ether, 4-(1-ethoxyvinyl)-3,3,5,5-tetramethylcyclohexanone, 2-butoxyethyl vinyl ether, divinyl ether, 1,3-divinyloxy-2,2-dimethylpropane, 4-vinyloxybutanol, diethyleneglycol divinyl ether, 4-(vinyloxymethyl)cyclohexylmethanol, isopentyl vinyl ether, diethyleneglycol monovinyl ether, n-butyl vinyl ether, 1,4-bis(2-vinyloxyethyl)benzene, hexanediol divinyl ether, 1-methoxy-1,3-butadiene, decyl vinyl ether, 4-(allyloxymethyl)-1,3-dioxolan-2-one, 1,1-diethylpropyl vinyl ether, 2-methoxyvinyl benzene, octyl vinyl ether, bis(vinyloxy)methane, 1,4-dimethoxy-1,3-butadiene, 2,3-dimethoxy-1,3-butadiene, triethyleneglycol divinyl ether, pentyl vinyl ether, octadecyl vinyl ether, 2-methoxypropene, triethyleneglycol methyl vinyl ether, 2,3-epoxypropyl vinyl ether, dodecyl vinyl ether, 1,1-bis(vinyloxy) butane, hexyl vinyl ether,6-vinyloxyhexanol, (z)-1-methoxy-1-buten-3-yne, phenyl vinyl ether, 2-ethylhexyl vinyl ether, poly-THF-divinyl ether, pluriol-E-200-divinyl ether, trimethylolpropane trivinyl ether, aminopropyl vinyl ether, 2-diethylaminoethyl vinyl ether, 2-ethoxy propene, 2-isobutoxypropene, 2-ethoxy-2-butene, 2-isobutoxy-2-propene, and ethyl propenyl ether. It is noted that if a divinyl ether is used, that products will be formed that have two moieties of formula IV that are linked through the mutual $R_4$ group.

Examples of trisubstituted and cyclic alkyl vinyl ethers are 1-methoxy-2-methyl cyclohexene and 2-methoxy-2-methyl-2-butene. Examples of the cyclic alkyl vinyl ethers are 2-methyl-2,3-dihydrofuran, 2,3-dihydrofuran, 2-methyl-3,4-dihydropyran, 3,4-dihydropyran, and 1-methoxy cyclohexene.

Examples of acetals according to general formula Vb are 2,2-dimethoxypropane, 2,2-diethoxypropane, 1,1-dimethoxybutane, 2-propyl-1,3-dioxolane, 1,1-dimethoxyethane, 1,1-diethoxyethane, 1,1-diethoxypropane, and 1,1-dimethoxycyclohexane.

The alkyl vinyl ether or acetal addition reaction is carried out under conditions conventional for this type of addition reaction. The temperature generally is in the range of 0–50° C. and preferably is between 10–25° C. The reaction is carried out in the presence of an acid catalyst. The amount of acid catalyst generally is 0.01–30 g/mole and preferably 0.1–15 g/mol of monoperoxy ester or monoperoxy carbonate.

The acid catalyst for the process is a conventional acidic catalyst such as a $C_1$–$C_{10}$ alkane or aryl sulphonic acid, a halogenated $C_1$–$C_{10}$ alkane sulphonic acid or a mixture of one or more of these compounds. The preferred catalysts for use are, but are not limited to, p-toluenesulfonic acid and methane sulfonic acid.

The invention further relates to these mixed peroxides as such having the general formula IV:

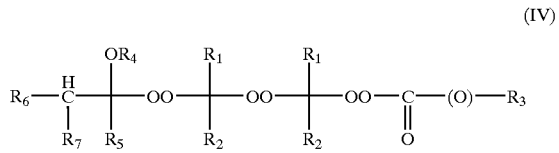

wherein $R_1$, $R_2$, $R_3$, $R_4$, $R_5$, $R_6$, and $R_7$ have the identified meaning. These mixed peroxides are obtainable with the above alkyl vinyl ether addition reaction.

The present invention further relates to a process for the preparation of a mixed diperoxy ester and a peroxy ester peroxy carbonate having the general formula VI:

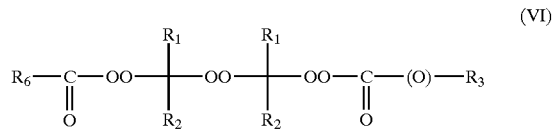

wherein $R_1$ and $R_2$ are independently selected from the group comprising hydrogen, $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, or $R_1$ and $R_2$ form a cycloalkyl group, which groups may include linear or branched alkyl moieties, and each of $R_1$ and $R_2$ may optionally be substituted with one or more groups selected from hydroxy, alkoxy, linear or branched alkyl, aryloxy, halogen, ester, carboxy, nitrile, and amido, and $R_3$ and $R_8$ are mutually different and independently selected from the group comprising $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, which groups may include linear or branched alkyl moieties, and each of $R_3$ and $R_8$ may optionally be substituted with one or more groups selected from hydroxy, alkoxy, linear or branched alkyl, aryloxy, halogen, ester, carboxy, nitrile, and amido, in which process a monoperoxy ester or monoperoxy carbonate with the general formula I:

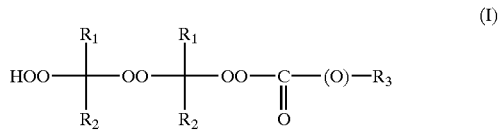

wherein $R_1$, $R_2$, and $R_3$ have the identified meaning is reacted with a carboxylic acid anhydride with the general formula VII:

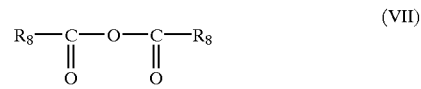

wherein $R_8$ has the identified meaning, in the presence of catalyst.

In the preparation process of these mixed diperoxy esters and peroxy ester peroxy carbonates the carboxylic acid anhydride has the general formula VII:

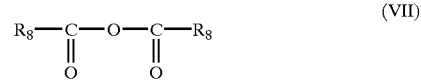

wherein $R_8$ has the identified meaning.

Suitable carboxylic acid anhydrides are those derived from the following carboxylic acids: acetic acid, phenylacetic acid, phenoxyacetic acid, propanoic acid, isobutyric acid, benzoic acid, 2-methyl-benzoic acid, 2-methylbutanoic acid, 2-butenoic acid, 3-phenylpropenic acid, 2,2-dimethylpropanoic acid, 2,2-dimethylbutanoic acid, 2,2-dimethylpentanoic acid, 2-ethylbutanoic acid, 3,5,5-trimethylhexanoic acid, 2-ethylhexanoic acid, neohexanoic acid, neoheptanoic acid, neodecanoic acid, octanoic acid, nonanoic acid, lauric acid, 3,5,5-trimethylpentanedioic acid, hexanedioic acid, 3,5,5-trimethylhexanedioic acid, 2,4,4-trimethylhexanedioic acid, decanedioic acid, undecanedioic acid, dodecanedioic acid, cyclohexanecarboxylic acid, 1,4-cyclohexanedicarboxylic acid, cyclohexane-1,4-diacetic acid, maleic acid, citric acid, 3-hydroxybutanoic acid, 4-hydroxybutanoic acid, 2-hydroxy-pentanoic acid, 3-hydroxypentanoic acid, 4-hydroxypentanoic acid, 5-hydroxypentanoic acid, hydroxyacetic acid, 2-hydroxyisobutyric acid, 2-hydroxypropanoic acid, 2-hydroxyhexanoic acid, hydroxypivalic acid, hydroxysuccinic acid, succinic acid, methylsuccinic acid, citraconic acid, fumaric acid, itaconic acid, oxalic acid, terephthalic acid, propenoic acid, and phthalic acid, and their corresponding methyl esters, ethyl esters, n-propyl esters, isopropyl esters, n-butyl esters, sec-butyl esters, isobutyl esters, ethylene glycol esters, and propylene glycol esters, and the halogen substituted carboxylic acids.

The reaction of the monoperoxy ester or monoperoxy carbonate with the carboxylic acid anhydride is carried out under conditions conventional for this type of reaction.

The temperature is in the range of 0–50° C., preferably between 10–25° C. The reaction is carried out in the presence a catalyst.

The amount of catalyst generally is 0.01–30 g/mole and preferably 0.1–15 g/mol of the monoperoxy ester or monoperoxy carbonate. The catalyst may be a basic catalyst or an acid catalyst.

The acid catalyst for the process is a conventional acidic catalyst such as a $C_1$–$C_{10}$ alkane or aryl sulphonic acid, a halogenated $C_1$–$C_{10}$ alkane sulphonic acid or a mixture of one or more of these compounds. The preferred catalysts for use are, but are not limited to, p-toluenesulfonic acid and methane sulfonic acid.

Examples of a suitable basic catalyst are sodium acetate, potassium acetate, sodium carbonate, potassium carbonate, sodium hydroxide, and potassium hydroxide.

In addition, the present invention includes the following mixed diperoxy esters and peroxy ester peroxy carbonates having the general formula VI:

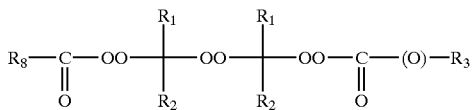

(VI)

wherein $R_1$, $R_2$, $R_3$, and $R_8$ have the identified meaning.

These mixed diperoxy esters and peroxy ester peroxy carbonates are obtainable with the above preparation process using a carboxylic acid anhydride as a reactant.

The present invention further relates to a process for the preparation of a mixed diperoxy carbonate having the general formula VIII:

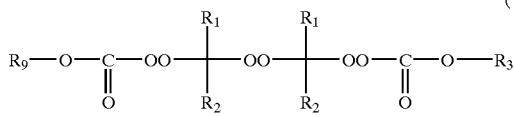

(VIII)

wherein $R_1$ and $R_2$ are independently selected from the group comprising hydrogen, $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, or $R_1$ and $R_2$ form a $C_3$–$C_{12}$ cycloalkyl group, which groups may include linear or branched alkyl moieties, and each of $R_1$ and $R_2$ may optionally be substituted with one or more groups selected from hydroxy, alkoxy, linear or branched alkyl, aryloxy, halogen, ester, carboxy, nitrile, and amido, and $R_3$ and $R_9$ are independently selected from the group comprising $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, which groups may include linear or branched alkyl moieties, and $R_3$ and $R_9$ may optionally be substituted with one or more groups selected from hydroxy, alkoxy, linear or branched alkyl, aryloxy, halogen, ester, carboxy, nitrile, and amido, which process comprises the reaction of the monoperoxy carbonate with the general formula I':

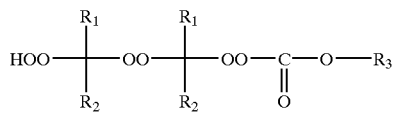

(I')

wherein $R_1$ and $R_2$ have the identified meaning, with halogen formate with the general formula III':

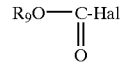

(III')

wherein $R_9$ has the identified meaning, with the proviso that $R_9$ is not identifical with $R_3$.

The monoperoxy carbonate used is obtainable by the above-described preparation process. Suitable halogen formates are those generally and specifically described in relation to this preparation process for monoperoxy carbonate. Preferably, the reaction is carried out in a suitable solvent.

Generally, the process is as claimed in claim 13, where the equivalent amount of acid halogen or halogen formate is in the range of 1–5 equivalents, preferably 3.0–5.0 equivalents. These numbers of equivalents are selected such that the chemical yield is optimal.

In general, the same reaction conditions may be used as for the monoperoxy carbonates preparation process.

Finally, the invention relates to mixed diperoxy carbonate having the general formula VIII:

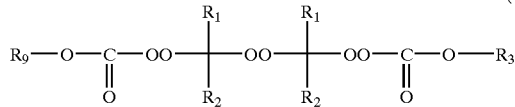

(VIII)

wherein $R_1$, $R_2$, $R_3$ and $R_9$ have the identified meaning, which is obtainable with the above preparation process.

The peroxides according to the present invention and produced with the preparation processes according to the present invention may be used as initiators for polymer production and in particular for the preparation of poly (vinylchloride), acrylic (co)polymers, polystyrene, polyethylene, for curing unsaturated polyester resins, and for polymer modification (such as grafting of monomers).

In the present invention, the polymerization is conducted by any conventional process, except that a specified radical polymerization initiator (or composition) is used. The polymerization processes may be carried out in the usual manner, for example in bulk, suspension, emulsion or solution. In the case of the production of ethylene (co)polymers, the reaction is usually carried out under high pressure, e.g. about 1000 to about 3500 bar.

The amount of initiator, which varies depending on the polymerization temperature, the capacity for removing the heat of polymerization, and, where applicable, the kind of monomer to be used and the applied pressure, should be an effective amount for achieving polymerization. Usually, from 0.001–25% by wt of peroxide, based on the weight of the (co)polymer, is employed. Preferably, from 0.001–20% by wt of peroxide is employed and most preferably from 0.001–15% by wt.

For most reactions within the present invention the polymerization temperature usually is 30° to 350° C., preferably 40° to 300° C. In general, if the temperature is below 30° C., the polymerization time becomes too long. However, when it exceeds 350° C., the radical polymerization initiator is spent in the initial stage of the polymerization, making it difficult to attain a high conversion. In order to reduce the amount of unreacted monomer, however, it is also possible to conduct polymerization using a temperature profile, e.g., to perform the initial polymerization at below 100° C. and then elevate the temperature above 100° C. to complete the polymerization. These variations are all known to the man skilled in the art, who will have no difficulty selecting the reaction conditions of choice, depending on the particular polymerization process and the specific radical polymerization initiator to be used.

Suitable monomers for polymerization using the ketone peroxides according to the present invention are olefinic or ethylenically unsaturated monomers, for example substituted or unsubstituted vinyl aromatic monomers, including styrene, alpha-methylstyrene, p-methylstyrene, and halogenated styrenes; divinylbenzene; ethylene; ethylenically unsaturated carboxylic acids and derivatives thereof, such as (meth)acrylic acids, (meth)acrylic esters, butylacrylate, hydroxyethyl (meth)acrylate, methylmethacrylate, 2-ethylhexyl acrylate, 2-ethylhexyl methacrylate, and glycidyl methacrylate; ethylenically unsaturated nitriles and amides, such as acrylonitrile, methacrylonitrile, and acrylamide; substituted or unsubstituted ethylenically unsaturated monomers, such as butadiene, isoprene, and chloroprene; vinyl esters, such as vinyl acetate and vinyl propionate; ethylenically unsaturated dicarboxylic acids and their derivatives including mono- and diesters, anhydrides and imides, such as maleic anhydride, citraconic anhydride, citraconic acid, itaconic acid, nadic anhydride, maleic acid, fumaric acid, aryl, alkyl and aralkyl citraconimides and maleimides; vinyl halides, such as vinyl chloride and vinylidene chloride; vinyl ethers, such as methylvinyl ether and n-butylvinyl ether; olefins, such as isobutene and 4-methylpentene; allyl compounds, such as (di)allyl esters, for example diallyl phthalates, (di)allyl carbonates, and triallyl (iso)cyanurate.

During (co)polymerization, the formulations may also contain the usual additives and fillers. As examples of such additives may be mentioned: stabilizers such as inhibitors of oxidative, thermal or ultraviolet degradation, lubricants, extender oils, pH controlling substances, such as calcium carbonate, release agents, colourants, reinforcing or non-reinforcing fillers such as silica, clay, chalk, carbon black, and fibrous materials, such as glass fibres, plasticizers, diluents, chain transfer agents, accelerators, and other types of peroxides. These additives may be employed in the usual amounts.

Finally, the polymerization process of the present invention can be employed to introduce functional groups into the (co)polymers. This may be accomplished by employing a peroxide which contains one or more functional groups attached thereto. These functional groups remain intact in the free radicals formed by the ketone peroxides and thus are introduced into the (co)polymer. Conventional polymerization conditions and equipment may be used to achieve this object of the present invention.

The peroxides according to the invention which may be used as a curing agents for the unsaturated polyesters and unsaturated polyester resins according to the present invention usually include an unsaturated polyester and one or more ethylenically unsaturated monomers. Suitable polymerizable monomers include styrene, alpha-methylstyrene, p-methylstyrene, chlorostyrenes, bromostyrenes, vinylbenzyl chloride, divinylbenzene, diallyl maleate, dibutyl fumarate, triallyl phosphate, triallyl cyanurate, diallylphthalate, diallyl fumarate, methyl (meth)acrylate, n-butyl (meth)acrylate, ethyl acrylate, and mixtures thereof which are copolymerizable with the unsaturated polyesters. The unsaturated polyesters are, for example, polyesters as they are obtained by esterifying at least one ethylenically unsaturated di- or polycarboxylic acid, anhydride or acid halide, such as maleic acid, fumaric acid, glutaconic acid, itaconic acid, mesaconic acid, citraconic acid, allylmalonic acid, tetrahydrophthalic acid, and others, with saturated and unsaturated di- or polyols, such as ethylene glycol, diethylene glycol, triethylene glycol, 1,2- and 1,3-propanediols, 1,2-, 1,3-, and 1,4-butanediols, 2,2-dimethyl-1,3-propanediols, 2-hydroxymethyl-2-methyl-1,3-propanediol, 2-buten-1,4-diol, 2-butyn-1,4-diol, 2,4,4-trimethyl-1,3-pentanediol, glycerol, pentaerythritol, mannitol, and others. The di- or polycarboxylic acids may be partially replaced by saturated di- or polycarboxylic acids, such as adipic acid, succinic acid, and others, and/or by aromatic di- or polycarboxylic acids, such as phthalic acid, trimellitic acid, pyromellitic acid, isophthalic acid, and terephthalic acid. The acids used may be substituted with groups such as halogen. Suitable halogenated acids include, for example, tetrachlorophthalic acid and tetrabromophthalic acid.

The peroxides of the present invention are suited for use in the modification of polymers such as degradation, crosslinking or grafting. More particularly, these peroxides can be employed in processes for grafting monomers onto polymers such as polyolefins and elastomers, and for the functionalization of polyolefins in the case of functional group-containing ketone peroxides of the present invention.

In general, the peroxide may be brought into contact with the (co)polymer in various ways, depending upon the particular object of the modification process. The polymer material may be in the solid state, molten state, in the form of a solution in the case of an elastomer, in a plastic state or in any physical form including finely divided particles (flake), pellets, film, sheet, in the melt, in solution, and the like. Polymers may also be in the liquid form, e.g. liquid rubbers.

In general, any (co)polymer comprising abstractable hydrogen atoms, in particular polyolefins, can be modified by the present process.

The amount of peroxide used in the modification process of the present invention should be an effective amount for achieving significant modification of the (co)polymer when treating a (co)polymer. More particularly, from 0.001–15.0 weight percent of peroxide, based on the weight of the (co)polymer, should be employed. More preferably, from 0.005–10.0% by wt percent is employed. Most preferably, an amount of 0.01–5.0% by wt is employed.

The peroxide may also be used for the modification of a chemical, whereby said chemical is reacted with the radicals formed upon decomposition of the peroxide, or with non-radical decomposition products that are formed when the peroxide is decomposed. As indicated above for the modification of polymers, the modification of chemicals will often, but not necessarily, involve the abstraction of protons from said chemical. An example of a modification reaction is the epoxidation of olefinically unsaturated compounds.

It is noted that in the preparation processes the ketone peroxide may be pure (T3) peroxide (as shown in the general formula II) or may comprise 5%–30%, such as 5%–25% and 10%–15%, of the (T3) derived peroxide, (T4), having the general formula II':

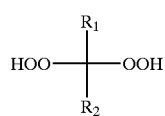

(II')

wherein $R_1$ and $R_2$ have the identified meaning. The presence of the corresponding T4 peroxide has no effect the on peroxide's use as polymerization initiator, curing agent, and modifying agent.

The peroxides can be prepared, transported, stored, and applied in the form of powders, granules, pellets, pastilles, flakes, slabs, pastes, solid masterbatches, and liquids. These formulations may have the form of a dispersion, such as a suspension or an emulsion. They can be be phlegmatized if necessary, depending on the particular peroxide and its concentration in the formulation. Which of these forms is to be preferred depends partly on the application for which it will be used and partly on the manner in which it will be mixed. Also, considerations of safety may play a role to the extent that phlegmatizers may have to be incorporated into certain compositions to ensure their safe handling. The formulations of the present invention are transportable, storage stable, and contain 1.0–90% by wt of one or more peroxides according to the present invention. Transportable means that the formulations of the present invention have passed the pressure vessel test (PVT). Storage stable means that the formulations of the present invention are both chemically and physically stable during a reasonable storage period under standard conditions.

More preferred formulations in accordance with the present invention contain 10–70% by wt of one or more of the ketone peroxides, most preferably these formulations contain 20–60% by wt of the ketone peroxides.

The formulations of the present invention can be liquids, solids or pastes depending on the melting point of the peroxide and the diluent employed. Liquid formulations can be made using liquid phlegmatizers for the ketone peroxide, liquid plasticizers, organic peroxides, and mixtures thereof as the diluent. The liquid component is generally present in an amount of 1–99% by wt of the composition, preferably 10–90% by wt, more preferably 30–90% by wt, and most preferably 40–80% by wt of the liquid formulation consists of liquid diluents.

It should be noted that certain phlegmatizers may not be suitable for use with all of the ketone peroxides of the present invention. More particularly, in order to obtain a safe composition, the phlegmatizer should have a certain minimum flash point and a boiling point relative to the decomposition temperature of the ketone peroxide such that the phlegmatizer cannot be boiled off leaving a concentrated, unsafe ketone peroxide composition behind. Thus, the lower-boiling phlegmatizers mentioned below may only be useful, for example, with particular substituted ketone peroxides of the present invention which have a low decomposition temperature.

In liquid formulations a liquid carrier or diluent is used. Preferably, this carrier or diluent is a solvent. For the monoperoxy esters and monoperoxy carbonates according to the present invention both polar and apolar solvents may be used. For the diperoxy esters, diperoxy carbonates, and mixed diperoxides only apolar solvents are used. Examples of the solvents are those given for the preparation of the various ketone peroxides.

In the solid and/or paste formulations of the present invention solid carrier materials are employed. Examples of such solid carriers are low-melting solids, such as dicyclohexylphthalate, dimethyl fumarate, dimethylisophthalate, triphenylphosphate, glyceryltribenzoate, trimethylolethane tribenzoate, dicyclohexylterephthalate, paraffinic waxes, dicyclohexylisophthalate, polymers, and inorganic supports. Inorganic supports include materials such as fumed silica, precipitated silica, hydrophobic silica, chalk, whiting, surface-treated clays such as silane-treated clays, calcined clays, and talc.

Polymers useful in the formulations of the present invention include polyethylene, polypropylene, ethylene/propylene copolymers, ethylene/propylene/diene monomer terpolymers, chlorosulphonated polyethylene, chlorinated polyethylene, polybutylene, polyisobutylene, ethylene/vinyl acetate copolymers, polyisoprene, polybutadiene, butadiene/styrene copolymers, natural rubber, polyacrylate rubber, butadiene/acrylonitrile copolymers, acrylonitrile/butadiene/styrene terpolymers, silicone rubber, polyurethanes, polysulphides, solid paraffins, and polycaprolactone.

Storage stable formulations must be both physically and chemically stable. By physically stable formulations are meant those formulations which do not suffer from significant phase separation upon storage. The physical stability of the present formulations can, in some instances, be improved by the addition of one or more thixotropic agents selected from cellulose esters, hydrogenated castor oil, and fumed silica. Examples of such cellulose esters are the reaction products of cellulose and acid compounds selected from, for example, acetic acid, propionic acid, butyric acid, phthalic acid, trimellitic acid, and mixtures thereof.

By chemically stable formulations are meant those formulations which do not lose a significant amount of their active oxygen content upon storage. The chemical stability of the present formulations can, in some instances, be improved by the addition of one or more known additives including sequestering agents such as dipicolinic acid and/or antioxidants such as 2,6-di(t-butyl)-4-methyl phenol and para-nonyl phenol.

The formulations of the present invention may also contain optional other additives as long as these do not have a significant adverse effect on the transportability and/or storage stability of the formulations. As examples of such additives may be mentioned: anti-caking agents, free-flowing agents, anti-ozonants, anti-oxidants, anti-degradants, U.V. stabilizers, coagents, fungicides, antistats, pigments, dyes, coupling agents, dispersing aids, blowing agents, lubricants, process oils, and mould-release agents. These additives may be employed in their usual amounts.

The ketone peroxides according to the invention may also be used as a dispersion, preferably in a polar medium. The medium in which the initiator according to the invention is dispersed should be inert towards the initiator and so polar that the initiator will hardly dissolve in it. The initiator preferably is dispersed in water or an alcohol. Most preferable is a dispersion in water. The use of such a medium makes for comparatively easy removal of any remnant, for example after the modification of the (co)polymer if so desired. Furthermore, the use of water or alcohols is attended with far fewer organoleptic and other drawbacks than the use of organic diluents, such as toluene and xylene, which has been common up to now.

As is well-known to the skilled person, the use of other adjuvants in initiator dispersions may be advisable or even essential in order to ensure the dispersion's chemical and/or physical stability for a sufficiently long period of time. For instance, if the storage temperature of the initiator dispersion is lower than the freezing point of the medium in which the initiator is dispersed, an appropriate freezing point depression agent can be added to counteract freezing. Also, a wide range of substances can be used for altering the rheology of the formulation. To this end generally use is made of one or more surface-active materials and one or more thickeners. If so desired, other additives may be incorporated into the formulation. As examples of such additives may be mentioned pH buffers, biocides, chemical stabilizers which counteract premature decomposition of the initiator, and anti-agers which counteract particle size growth in the dispersion.

Using mixtures of monoperoxy esters or monoperoxy carbonates with other peroxides, for example diperoxy esters or diperoxy carbonates, a wide range of reactivities can be achieved. The half-life time of the mixture of the different peroxides normally lies between the half-life of each of the pure peroxides. This is useful for example in ethylene polymerization, where the optimum efficiency of the peroxide (mixture) in the polymerization process is very dependent on the reactivity of the peroxide (mixture).

The following examples illustrate the preparation processes for the monoperoxy ester, mixed diperoxy carbonate, monoperoxy carbonate, mixed diperoxy esters, peroxy ester peroxy carbonates, and mixed peroxides according to the present invention and their applications.

EXAMPLE 1

Preparation of 1-(2-ethylhexanoylperoxy)-1,3-dimethylbutylperoxy-1,3-dimethylbutyl hydroperoxide In to a 250 ml beaker were charged 75 g of methylisobutylketone peroxide in isododecane (containing 0.0007 mole T4 and 0.0970 mole (T3) and 20 g of NaCl-25%. The pH was adjusted to 13.5 with KOH-45% at a temperature of 8–12° C.

Next 16.3 g of 2-ethylhexanoylchloride (0.10 mole; 1 eq) were dosed in 15 min. simultaneously with lye, keeping the pH at >13.5. The mixture was stirred for another 90 min. at 3–5° C.

After separation of the water layer the organic layer was washed with NaOH-4N and $NaHCO_3$-6%. The product was dried over magnesium sulphate.

Yield 80.5 g of product with an active oxygen content of 5.78%. (chemical yield:99%).

Ratio mono:bis=92:8.

EXAMPLE 2

As example 1, but with a ratio of 2.1 moles of 2-ethylhexanoyl chloride to 1 mole of methylisobutylketone peroxide in isododecane. Here the product also was the monoperoxy ester. Ratio mono:bis=88:12.

EXAMPLE 3

Preparation of 1-(1-(2 ethylhexanoylperoxy)-1-methylpropylperoxy)-1-methylpropyl hydroperoxide As in example 1, but using methylethylketone peroxide instead of methylisobuthylketone peroxide. Chemical yield 89%. Ratio mono:bis=70:30

EXAMPLE 4

Preparation of 1-(1-(2-methylpropanoylperoxy)-1,3-dimethylbutylperoxy-1,3-dimethylbutyl hydroperoxide.

In to a 250 ml beaker were charged 25 g of methylisobutylketone peroxide in isododecane (containing 0.0005 mole T4 and 0.0340 mole T3) and 7 g of NaCl-25%. The pH was adjusted to 13.5 with KOH-45% at a temperature of 8–12° C.

Next 3.7 g of isobutyrylchloride (0.0347 mole; 1 eq) were dosed in 15 min. simultaneously with the lye, keeping the pH at >13.5. The mixture was stirred for another 90 min. at 3–5° C.

After separation of the water layer the organic layer was washed with water and $NaHCO_3$-6%. The product was dried over magnesium sulphate.

Yield 24.5 g of product with an active oxygen content of 6.10%. (chemical yield:90%).

Ratio mono:bis=88:12.

EXAMPLE 4A

Preparation of 1-Hydroperoxy-1,2-dimethylpropyl 1-(2-methylpropanoylperoxy)-1,2-dimethylpropyl peroxide As example 4, but by using 50 g methylisopropylketone peroxide in isododecane.

Yield 49.1 g with AO 5,69% (Chemical Yield 78%).

EXAMPLE 5

Preparation of 1-(1-(2,2-dimethylpropanoylperoxy)-1,3-dimethylbutylperoxy)-1,3-dimethylbutyl hydroperoxide Into a 250 ml beaker were charged 25 g of methylisobutylketone peroxide in isododecane (containing 0.0005 mole T4 and 0.0340 mole T3) and 7 g of NaCl-25%. The pH was adjusted to 13.5 with KOH-45% at a temperature of 8–12° C.

Next 4.2 g of pivaloyl chloride (0.0347 mole; 1 eq) were dosed in 15 min. simultaneously with the lye, keeping the pH at >13.5. The mixture was stirred for another 90 min. at 3–5° C.

After separation of the water layer the organic layer was washed with water and $NaHCO_3$-6%. The product was dried over magnesium sulphate.

Yield 24.5 g of product with an active oxygen content of 6.10%. (chemical yield:90%).

Ratio mono:bis=97:3.

EXAMPLE 6

As example 5 but with a ratio of 2.1 moles of pivaloyl chloride to 1 mole of methylisobutylketone peroxide in isododecane. Here the major product also was the monoperoxyester. Ratio mono:bis=65:35.

EXAMPLE 7

Preparation of 1-(1-(2,2-dimethylpropanoylperoxy)-1-methylpropylperoxy)-1-methylpropyl hydroperoxide As example 6, but with a ratio of 2.1 moles of pivaloyl chloride to 1 mole of methylethylketone peroxide in isodecane. Here the major product also was the monoperoxy ester. Ratio mono:bis=60:40.

EXAMPLE 8

Preparation of 1-(1-isopropoxycarbonylperoxy)-1,3-dimethylbutylperoxy-1,3-dimethylbutyl hydroperoxide Into a 250 ml beaker were charged 30 g of methylisobutylketone peroxide in isododecane (containing 0.0003 mole T4 and 0.0404 mole T3) and 70 ml pentane. To this mixture 6.5 g pyridine were added at a temperature of 8–12° C.

Next 10 g of isopropyl chloroformate (0.0814 mole; 2.0 eq)) were dosed in 10 min. at a temperature of 6–8° C. The mixture was stirred for another 60 min. at 4–6° C.

The reaction mixture was poured into an ice/water mixture and the organic layer was separated and washed twice with H2SO4-2N, once with NaOH-4N, and once with water.

The product was dried over magnesium sulphate and the pentane was evaporated.

Yield 28.6 g of product with an active content oxygen of 5.83%. (chemical yield:90%).

Ratio mono:bis=50:50.

EXAMPLE 9

Preparation of 1-acetylperoxy-1,3-dimethylbutyl-1-(2-ethylhexanoylperoxy) 1,3-dimethylbutyl peroxide.

Into a 50 ml beaker were charged 10 g of 1-(2-ethylhexanoylperoxy)-1,3-dimethylbutylperoxy-1,3-dimethylbutyl hydroperoxide (0.00973 mole) and 2 g of acetic anhydride (0.0195 mole) at a temperature of 15° C. To this mixture 0.5 g potassium carbonate acid was added slowly, keeping the temperature at 15–20° C. The mixture was stirred for another 60 min. at 20° C., washed twice with water, once with $NaHCO_3$-6% and dried over magnesium sulphate.

Yield 10 g of product with an active oxygen content of 3.20% (chemical yield:66%).

EXAMPLE 9A

Preparation of 1-Acetylperoxy-1,3-dimethylbutyl-1-(2-methylpropanoylperoxy)-1,3-dimethyl peroxide As example 9, but by using 25 g of 1-(1-(2-Methylpropanoylperoxy)-1,3-dimethylbutylperoxy-1,3-dimethylbutyl hydroperoxide from example 4.

Yield 25.9 g with AO 7.90% (Chemical Yield 96%).

EXAMPLE 9B

Preparation of 1-Acetylperoxy-1,2-dimethylpropyl 1-(2-methylpropanoylperoxy)-1,2-dimethylpropyl peroxide As example 9, but by using 30 g of 1-Hydroperoxy-1,2-dimethylpropyl 1-(2-methylpropanoylperoxy)-1,2-dimethylpropyl peroxide from example 4A.

Yield 25.4 g with AO 5.26% (Chemical Yield 80%).

EXAMPLE 10

Preparation of 1-(2-ethylhexanoylperoxy)-1,3-dimethylbutyl-1-(1-isobutoxyethyl)peroxy 1,3-dimethylbutyl peroxide.

Into a 50 ml beaker were charged 20 g of 1-(2-ethylhexanoylperoxy)-1,3-dimethylbutylperoxy-1,3-dimethylbutyl hydroperoxide (0.0241 mole) and 0.2 g of p-toluenesulphonic acid monohydrate at a temperature of 20° C. Then 2.42 g of isobutylvinylether were dosed in 2 min., keeping the temperature at 10° C. by cooling with an icewater bath. The mixture was stirred for another 10 min. at 20° C., washed with $NaHCO_3$-6% and dried over magnesium sulphate.

Yield 20.6 g of product with an active oxygen content of 4.19% (chemical yield:75%).

EXAMPLE 11

Preparation of 1-(2,2-dimethylpropanoylperoxy)-1,3-dimethylbutyl, 1-((1-isobutoxyethyl)peroxy)-1,3-dimethylbutyl peroxide As example 10, but starting from the product obtained in example 5.

Chemical yield 80%.

EXAMPLE 12

As example 10, with the same result a mixture of 1-(2-ethylhexanoylperoxy)-1,3-dimethylbutylperoxy-1,3-dimethylbutyl hydroperoxide containing 10–25% 1-hydroperoxy-1,3-dimethylbutyl peroxy-2-ethylhexanoate was converted to the mixed peroxide.

EXAMPLE 13

Preparation of 1-(1-(1 isobutoxyethylperoxy)-1-methylpropyl peroxy 1-methylpropylperoxy-2-ethylhexanoate As in example 10, but using the hydroperoxide prepared in example 3 as starting material.

EXAMPLE 14

Preparation of 1-(1-acetylperoxy-1,3-dimethylbutylperoxy)-1,3-dimethylbutyl hydroperoxide
Into a 250 ml. beaker were charged 75 g of methylisobutylketone peroxide in isododecane (containing 0.0007 mole T4 with KOH-45% and 0.0970 mole T3) and 20 g of NaCl-25%. The pH was adjusted to 13.5 with KOH-45% at a temperature of 8–12° C.

The 7.9 g of acetyl chloride (0.10 mole) was dosed in 15 min. simultaneously with the lye, keeping the pH at >13.5. The mixture was stirred for another 90 min. at 3–5° C. After separation of the water layer the organic layer was washed with NaOH-4N and $NaHCO_3$-6%. The product was dried over magnesium sulphate. Yield 68.5 g of product with an active oxygen content of 6.4%. (chemical yield: 90%). This peroxide has a half life time of 1 h at 96° C. (determined with DSC). By mixing this product with its bis-adduct (having a t1/2 of 1 h at 84° C.) in a certain ratio, a half-life time of 1 h can be achieved between 84 and 96° C. For example a 50%:50% (mole/mole) mixture gives a half-life time of 1 h at 92° C.

EXAMPLE 15

Polymerization of vinyl chloride

Peroxyesters of the present invention with 1-hour half-life temperatures in the range of 40°–60° C. were evaluated with good results in vinyl chloride polymerization. The polyvinyl chloride was produced according to an experimental procedure to be used for the 5 liter autoclave, the conversion in time being measured via the "butane tracer technique' (ref.: T. Y. Xie, A. E. Hamielek, P. E. Wood, O. R. Woods and H. Westmijze, *J. Appl. Pol. Sci.*, Vol. 41 (1990)). A 5-liter stainless steel reaction vessel provided with: 1 baffle, a three-bladed stirrer, (n=450 rpm), a pressure transducer, a nitrogen purge, and the sampling device for the butane tracer technique, was charged with 2700 g demineralized water and 0,15% Gohsenol KP-08 (1.0125 g) on vinyl chloride, and with a buffer: 1 g $Na_2HPO_4$ ex Baker, no. 0303+1 g $Na_2HPO_4$ ex Baker no. 0306. The vessel was closed and pressurized with 15 bar nitrogen. The vessel was evacuated and pressurized with nitrogen (5 bar) at least three times. Subsequently, the vessel was fed the peroxy ester of the present invention identified in Table 1 as an initiator. The vessel was evacuated again and subsequently charged with vinyl chloride. The temperature was increased from ambient to the polymerization temperature (37–62° C.) in about 30 minutes (37 and 42° C.) and up to 60 minutes for the higher temperature (53/57/62° C.). After 10 min. polymerization time, polyvinyl alcohol was fed from a nitrogen pressurized bomb. The standard polymerization time was 8 hours. Before opening of the vessel atmospheric pressure was attained, and the vessel was evacuated for at least half an hour. The Polyvinyl chloride formed was filtered and washed on a glass filter (S2). Subsequently, the polyvinyl chloride was dried in a fluid bed dryer at 60° C.

The results are shown in Table 2.

TABLE 2 vinyl chloride polymerization with ketone peroxide according to the present invention.

| Peroxide | Temp °C. | perox % | yield % | CPT Min |
|---|---|---|---|---|
| Peroxide of example 11 | 42 | 0.12 | 88.2 | 287 |
| Peroxide of example 11 | 62 | 0.090 | 85.1 | 335 |
| Peroxide of example 12 | 62 | 0.098 | 98.8 | 165 |

% peroxy = mass % on VCM
CPT = constant pressure time: time unitl vinyl chloride pressure drop (about 75% conversion)

EXAMPLE 16

In order to determine the cure performance of the peroxy compounds according to the present invention as a curing agent for unsaturated polyester, a comparison was made with a conventional curing agent, tertiary butyl per 2-ethyl hexonoate (conventional compound).

The Time-Temperature curve was measured at 100° C. on compounds containing 100 parts of polyester resin, 150 parts of sand as filler, and 1 part of the curing agent. This procedure was carried out according to the method outlined by the Society of Plastic Institute. 25 g of compound were poured into a test tube and a thermocouple was inserted through the enclosure cork in the middle of the tube. The glass tube was then placed in the oil bath maintained at a specific test temperature and the time-temperature curve was measured. From the curve the following parameters were calculated:

Gel time (GT)=time in minutes elapsed between 16.7° C. below and 5.6° C. above the bath temperature.

Time to peak exotherm (TTP)=time elapsed between the start of the experiment and the moment the peak temperature is reached.

Peak exotherm (PE)=the maximum temperature reached.

The results are summarised in the following table:

| COMPOUND | TEST TEMP, °C. | GT, MIN. | TTP, MIN. | PE, °C. |
|---|---|---|---|---|
| Tert.butylperoxy 2-ethyl hexanoate | 100 | 0.87 | 3.4 | 197 |
| Example 10 | 100 | 0.15 | 2.57 | 196 |
| Example 3 | 100 | 0.2 | 2.33 | 190 |
| Example 12 | 100 | 0.28 | 2.35 | 195 |

All peroxy compounds according to the present invention showed a faster reactivity in terms of gel time and time to peak.

What is claimed is:

1. A process for the preparation of the mixed peroxy ester or mixed peroxy carbonate having the formula IV, with the oxygen in parentheses being absent for the peroxy ester and present for the peroxy carbonate:

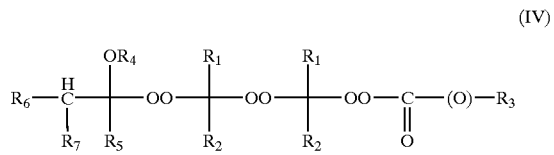

(IV)

wherein $R_1$, $R_2$, $R_5$, $R_6$ and $R_7$ are independently selected from the group consisting of hydrogen, $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, or $R_1$ and $R_2$ form a $C_3$–$C_{12}$ cycloalkyl group, which alkyl groups may include linear or branched alkyl moieties, and each of $R_1$, $R_2$, $R_5$, $R_6$ and $R_7$ may optionally be substituted with one or more groups selected from hydroxy, alkoxy, linear or branched alkyl, aryloxy, halogen, ester, carboxy, nitrile, and amido, $R_3$ and $R_4$ are independantly selected from the group consisting of $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, which groups may include linear or branched alkyl moieties, and each of $R_3$ and $R_4$ may optionally be substituted with one or more groups selected from hydroxy, alkoxy, linear or branched alkyl, aryloxy, halogen, ester, carboxy, nitrile, and amido, any pair of the optionally substituted $R_4$, $R_5$, $R_6$ and $R_7$ may form a ring, which process comprises the reaction of the corresponding monoperoxy ester or monoperoxy carbonate with the formula I, with the oxygen in the parentheses being absent for the monoperoxy ester and present for the monoperoxy carbonate:

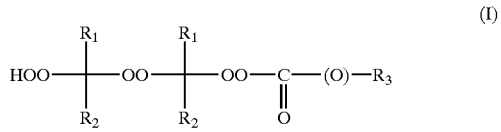

(I)

wherein $R_1$, $R_2$, and $R_3$ have the identified meaning, with an alkyl vinyl ether with the formula Va or with an acetal with the formula Vb:

(Va)

(Vb)

wherein $R_4$–$R_7$ have the same meanings as given above, in the presence of a catalyst.

2. A mixed peroxy ester or mixed peroxy carbonate having the formula IV, with the oxygen in parentheses being absent for the peroxy ester and present for the peroxy carbonate:

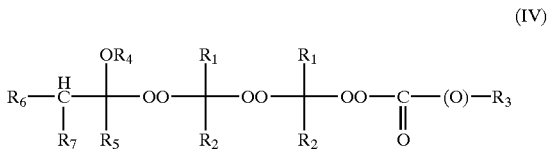

(IV)

wherein $R_1$, $R_2$, $R_3$, $R_4$, $R_5$, $R_6$ and $R_7$ have the meaning given in claim 1.

3. A mixed peroxide as claimed in claim 2 wherein $R_5$, $R_6$ and/or $R_7$ are hydrogen.

4. A process for the preparation of a mixed diperoxy ester and a peroxy ester peroxy carbonate having the formula VI, with the oxygen in parentheses being absent for the diperoxy ester and present for the peroxy ester peroxy carbonate:

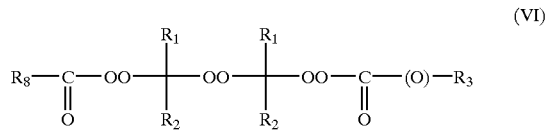

(VI)

wherein $R_1$ and $R_2$ are independently selected from the group consisting of hydrogen, $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, or $R_1$ and $R_2$ form a $C_3$–$C_{12}$ cycloalkyl group, which alkyl groups may include linear or branched alkyl moieties, and each of $R_1$ and $R_2$ may optionally be substituted with one or more groups selected from hydroxy, alkoxy, linear or branched alkyl, aryloxy, halogen, ester, carboxy, nitrile, and amido, and $R_3$ and $R_8$ are mutually different and independently selected from the group consisting of $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, which groups may include linear or branched alkyl moieties, and each of $R_3$ and $R_8$ may optionally be substituted with one or more groups selected from hydroxy, alkoxy, linear or branched alkyl, aryloxy, halogen, ester, carboxy, nitrile, and amido, in which process monoperoxy ester or monoperoxy carbonate with the formula I, with the oxygen in parentheses being absent for the monoperoxy ester and present for the monoperoxy carbonate:

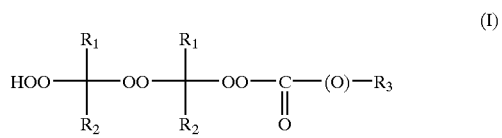

(I)

wherein $R_1$, $R_2$, and $R_3$ have the same meanings as given above, is reacted with a carboxylic acid anhydride with the formula VII:

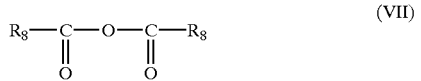

(VII)

in the presence of an acid catalyst.

5. A mixed diperoxy ester and peroxy ester peroxy carbonate having the formula VI, with the oxygen in parentheses being absent for the diperoxy ester and present for the peroxy ester peroxy carbonate:

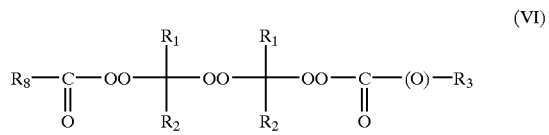

(VI)

wherein $R_1$, $R_2$, $R_3$, and $R_8$ have the meaning given in claim 4, with the proviso that $R_3$ and $R_8$ are each different if the oxygen atom, (O), is absent.

6. A process for the preparation of a mixed diperoxy carbonate having the formula VIII:

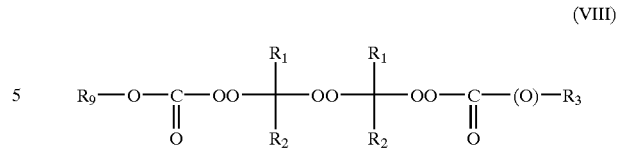

(VIII)

wherein $R_1$ and $R_2$ are independently selected from the group consisting of hydrogen, $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, or $R_1$ and $R_2$ form a $C_3$–$C_{20}$ cycloalkyl group, which alkyl groups may include linear or branched alkyl moieties, and each of $R_1$ and $R_2$ may optionally be substituted with one or more groups selected from hydroxy, alkoxy, linear or branched alkyl, aryloxy, halogen, ester, carboxy, nitrile, and amido, and $R_3$ and $R_9$ are independently selected from the group consisting of $C_1$–$C_{20}$ alkyl, $C_3$–$C_{20}$ cycloalkyl, $C_6$–$C_{20}$ aryl, $C_7$–$C_{20}$ aralkyl, and $C_7$–$C_{20}$ alkaryl, which groups may include linear or branched alkyl moieties, and $R_3$ and $R_9$ may optionally be substituted with one or more group selected from hydroxy, alkoxy, linear or branched alkyl, aryloxy, halogen, ester, carboxy, nitrile, and amido, which process comprises the reaction of the monoperoxy carbonate with the formula I':

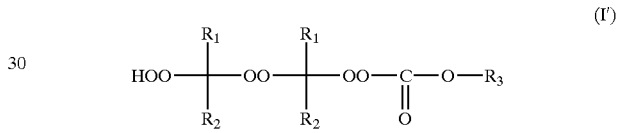

(I')

with a halogen formate with the formula III':

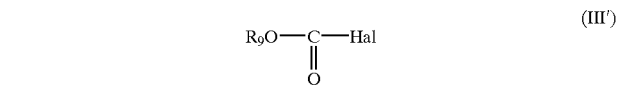

(III')

with the proviso that $R_9$ is not identical with $R_3$.

7. A process as claimed in claim 6 wherein the identical equivalent amount of halogen formate is in the range of 1–5 equivalents.

8. A mixed diperoxy carbonate having the formula VIII:

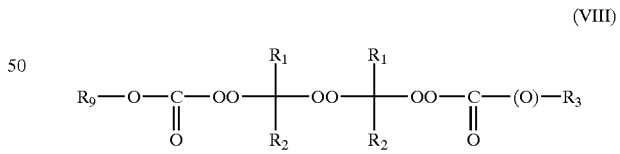

(VIII)

wherein $R_1$, $R_2$, $R_3$ and $R_9$ have the same meanings set forth in claim 6, with the proviso that that $R_3$ and $R_9$ are each different.

* * * * *